United States Patent [19]
Dell et al.

[11] Patent Number: 5,281,619
[45] Date of Patent: Jan. 25, 1994

[54] THERAPY FOR DIABETIC COMPLICATIONS

[75] Inventors: Colin P. Dell, Dorking; Colin W. Smith, Bracknell, both of England

[73] Assignee: Eli Lilly and Company, Indianapolis, Ind.

[21] Appl. No.: 34,011

[22] Filed: Mar. 22, 1993

Related U.S. Application Data

[63] Continuation-in-part of Ser. No. 951,629, Sep. 25, 1992.

[51] Int. Cl.$^5$ .............................................. A61K 31/35
[52] U.S. Cl. ...................................... 514/454
[58] Field of Search ........................................ 514/454

[56] References Cited

PUBLICATIONS

Elagamey, et al., *Indian Journal of Chemistry*, 29B, 885–886 (1990).
Elagamey, et al., *Collection Czechoslovak Chem. Commun.*, 53(7), 1534–1538 (1988).
Reaktionen, *Monatshefte für Chemie*, 110, 249–256 (1979).
Otto, et al., *Arch. Pharm.*, 312(6), 548–50 (1979).
Reaktionen *Monatshefte für Chemie*, 110, 115–119 (1979).

*Primary Examiner*—Bernard Dentz
*Attorney, Agent, or Firm*—Steven P. Caltrider; Leroy Whitaker

[57] ABSTRACT

This invention provides a method of treating diabetic complications in mammals which comprises the administration of a compound of the Formula I:

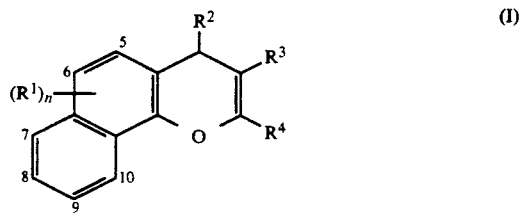

(I)

in which n, $R_1$, $R_2$, $R_3$, and $R_4$ are variables.

7 Claims, No Drawings

THERAPY FOR DIABETIC COMPLICATIONS

This application is a continuation in part of Dell et al. U.S. Ser. No. 951,629, filed Sep. 25, 1992.

BACKGROUND OF THE INVENTION

Diabetic complications, including diabetic retinopathy, nephropathy, and neuropathy are largely the result of abnormalities in microvascular function. Changes in vascular function include increased blood vessel permeability and altered blood flow. These changes precede the development of the clinical symptoms of diabetic complications.

Diabetic retinopathy and proliferative vitreoretinopathy are characterized by the growth of new blood vessels, or angiogenesis. One of the early events in angiogenesis is secretion of proteases involved in the dissolution of the basement membrane. These proteases include the plasminogen activators, procollagenase and prostromelysin. Plasminogen activators such as urokinase (uPA) and tissue plasminogen activator (tPA) are serine proteases which cleave the zymogen plasminogen to generate the active serine protease plasmin. Plasmin can influence basement membrane integrity directly through cleavage of basement membrane components or indirectly through cleavage of procollagenase and prostromelysin to generate active collagenase and stromelysin. The resulting dissolution of the basement membrane allows the endothelial cells to escape from the microvessel and begin the neovascularization process.

Increased plasmin formation also has several ramifications in terms of the permeability of the diabetic microvessel. Plasmin can directly degrade basement membrane components or can activate stromelysin, thus directly or indirectly influencing the normal turnover of heparan sulfate proteoglycan (HSPG). Because HSPG is involved in blood vessel permeability as well as growth control, this enhanced degradation of HSPG may result in its depletion from the membrane with resultant increased vessel permeability.

Microvascular dysfunctions arise through this abnormal activation of endothelial cells which is mediated, in part, through protein kinase C (PKC)-regulated pathways. See MacGregor, et al., *J Clin Invest*, 83: 90-94 (1988); Lee, et al., *Proc. Natl. Acad. Sci.*, 85: 5141-5145 (1989).

Agents that block or reverse the activation of endothelial cells and inhibit the alterations in microvessel function will have a beneficial effect in terms of preserving normal structure and function in the tissues affected by the complications of diabetes. The agents will improve the quality of life and longevity of diabetics.

The present invention discloses a method of inhibiting endothelial cell activation. Accordingly, the present invention provides a method of treating diabetic complications in mammals which comprises the administration of a compound of the Formula I:

This invention covers the use of these compounds in the treatment of diabetic complications, as well as in other disease states in which there is vascular dysfunction.

SUMMARY OF THE INVENTION

This invention provides a method of treating diabetic complications in mammals which comprises the administration to a patient in need of treatment a therapeutic dosage of a compound of the Formula I:

wherein
n is 0, 1 or 2;
$R^1$ is $C_1-C_4$ alkoxy, OH, or COOH attached at any of the positions 5, 6, 7, 8, or 9;
$R^2$ is phenyl, said phenyl being optionally substituted;
$R^3$ is nitrile, or $R_3$ is carboxy or —$COOR_8$ when $R_2$ is phenyl substituted with 3-nitro or 3-trifluoromethyl;
$R^4$ is —$NR^{12}R^{13}$, —$NHCOR^{12}$, —$N(COR^{12})_2$, or —$N=CHOCH_2R^{12}$;
$R^8$ is an ester group; and
$R^{12}$ and $R^{13}$ are each hydrogen or $C_{1-4}$ alkyl.

DETAILED DESCRIPTION AND PREFERRED EMBODIMENT

The synthesis of certain phenyl-substituted naphtho [1.2-b]pyrans is described by Elagamey A. et al. in Indian Journal of Chemistry, 29B, 885-886, (1990), and Collection Czechoslovak Chem. Commun., 53(7), 1534-1538, (1988). No biological properties or activity are ascribed to the compounds disclosed.

A substituted phenyl group is substituted with one or more, preferably one or two substituents each selected from halo, trifluoromethyl, $C_1-C_4$ alkyl, $C_{1-4}$ alkoxy, —$COOR^8$, trifluoromethoxy, or nitro. In addition, substituted phenyl includes a phenyl group in which neighboring atoms are substituted by —$O(CH_2)_mO$—, where m is 1, 2 or 3. Preferably phenyl is substituted with one substituent in position 3.

In the above formula (I), halo is, for example, fluoro, chloro or bromo. Halo is preferably chloro. A $C_{1-4}$ alkyl group includes, for example, methyl, ethyl, propyl and butyl, and is preferably methyl or ethyl. A $C_{1-4}$ alkoxy group is one such alkyl group linked through oxygen to an aryl nucleus.

The group $R^4$ is preferably —$NR^{12}R^{13}$, and especially —$NH_2$.

An especially preferred group of compounds is of the formula

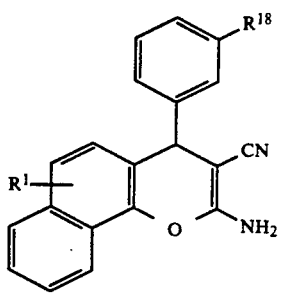

where $R^1$ is hydrogen, or $C_{1-4}$ alkoxy; and $R^{18}$ is nitro or trifluoromethyl. The $R^1$ group is preferably attached at the 5, 6 or 9 positions.

It will be appreciated that when, for example $R^3$ is —COOH, an opportunity exists for salts to be formed. They can be derived from any of the well known bases. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

In addition to pharmaceutically-acceptable salts, other salts are included in the invention. They may serve as intermediates in the purification of compounds or in the preparation of other, for example pharmaceutically-acceptable, acid addition salts, or are useful for identification, characterization or purification.

When $R^3$ is —COOR$^8$, the compounds are in ester form. The ester group can be any conventional group, for example, an ester derived from an alcohol, especially a $C_{1-4}$ alcohol. Preferred values of $R^8$ are thus $C_{1-4}$ alkyl.

It will be appreciated that the compounds of the invention contain an asymmetric carbon atom which gives rise to enantiomers. The compounds are normally prepared as racemates and can conveniently be used as such but individual enantiomers can be isolated by conventional techniques if so desired. Such racemates and individual enantiomers form part of the present invention.

The compounds disclosed in the present invention may be prepared as follows:
(1) reacting a compound of the formula

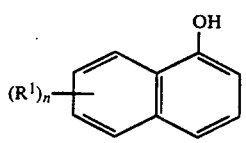

with a compound of the formula

to give a compound of formula (I) in which $R^4$ is —NH$_2$, or
(2) converting a compound of the formula

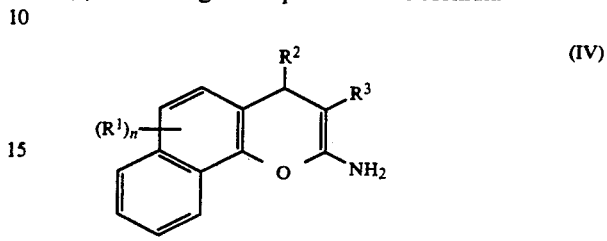

to a compound of formula (I) in which $R^4$ IS —NR$^{12}$R$^{13}$, —NHCOR$^{12}$, —N(COR$^{12}$)$_2$, —N=CHOCH$_2$R$^{12}$, With regard to process (1), the reaction is preferably carried out at a temperature of from 0° C. to 100° C. and in the presence of an organic solvent, such as for example ethanol. Compounds of formula (II) are known or can be easily synthesized by known methods.

The reactants of formula (III) can be prepared by reacting the appropriate nitrile of the formula $$R^3CH_2CN$$

with an aldehyde of the formula $$R^2CHO$$

preferably at a temperature of from 20° C. to 100° C. in the presence of an organic base as catalyst such as piperidine and in the presence of an organic solvent, such as for example ethanol. The nitrile and aldehyde reactants are known compounds or can be made by methods known in the art.

With regard to process (2), the free enamine can be prepared by reaction (1) and subsequently converted to compounds in which $R^4$ takes other values. For example, the free amino group can be alkylated with reagents of formula $R^{12}X$ or $R^{13}X$ where X is halogen, or $(R^{12})_2SO_4$ or $(R^{13})_2SO_4$ to give the mono- or dialkylated product. Similarly the amino group can be acylated with an acyl halide or an acid anhydride such as $R^{12}COX$ or $(R^{12}CO)_2O$ to give compounds in which $R^4$ is —NHCOR$^{12}$ or —N(COR$^{12}$)$_2$. Compounds in which $R^4$ is —N=CHOCH$_2$R$^{12}$ are prepared by reaction with the appropriate trialkyl orthoformate.

The preparation of representative compounds of the present invention is illustrated by the following Examples.

PREPARATIONS 3-(Trifluoromethyl)-benzaldehyde (9.2 g) and ethyl cyanoacetate (5.3 ml) were dissolved in ethanol (20 ml) and this solution was heated to reflux temperature. Heating was discontinued, piperidine (two drops) was added, and once the vigor of the reaction began to subside heating was recommenced and maintained at reflux temperature for one hour. The solution was chilled, using an ice-water bath, water (30 ml) was added and white crystals of ethyl 2-cyano-3-[3-(trifluoromethyl)-phenyl)]-propenoate were filtered off, washed with water and dried, m.p. 79° C.

The following compounds were prepared in a similar manner:

Ethyl 2-cyano-3-[4-(trifluoromethyl)phenyl]-propenoate, m.p. 114° C.
Ethyl 2-cyano-3-[2-(trifluoromethyl)phenyl]-propenoate, m.p. 74° C.
2-Nitrobenzylidenemalononitrile, m.p. 141° C.
3-Nitrobenzylidenemalononitrile, m.p. 108° C.
4-Nitrobenzylidenemalononitrile, m.p. 162° C.
3-Chlorobenzylidenemalononitrile, m.p. 118° C.
3-Fluorobenzylidenemalononitrile, m.p. 91° C.
3-Bromobenzylidenemalononitrile, m.p. 105° C.
2-(Trifluoromethyl)-benzylidenemalononitrile, m.p. 46° C.
3-(Trifluoromethyl)-benzylidenemalononitrile, m.p. 81° C.
4-(Trifluoromethyl)-benzylidenemalononitrile, m.p. 109° C.
4-(2,2-Dimethylethyl)-benzylidenemalononitrile, m.p. 92° C.
3-Pyridinecarboxalidemalononitrile, m.p. 89° C.
2-Thiophenecarboxalidemalononitrile, m.p. 98° C.
3-Methoxybenzylidenemalononitrile, m.p. 102° C.
3-Trifluoromethoxybenzylidenemalononitrile, m.p. 73° C.
3-Chloro-4-fluorobenzylidenemalononitrile, m.p. 111° C.
3-Bromo-4-fluorobenzylidenemalononitrile, m.p. 122.5° C.
3-Carbomethoxybenzylidenemalononitrile, m.p. 125° C.
3-Hydroxybenzylidenemalononitrile, m.p. 152° C.
2-Cyano-(3-nitrophenyl)propenamide, m.p. 140° C.
3,4-Dichlorobenzylidenemalonitrile, m.p. 154° C.
3,4-Dimethoxybenzylidenemalonitrile, m.p. 137° C.
3,4-(Methylenedioxy)benzylidenemalonitrile, m.p. 201°–202° C.
4-Chloro-3-nitrobenzylidenemalonitrile, m.p. 142° C.
2-Nitro-4-thiophenecarboxalidemalonitrile, m.p. 103–104° C.
α-Methanesulphonyl-3-nitrocinnamonitrile, m.p. 157° C.
4-Fluoro-3-nitrobenzylidenemalonitrile, m.p. 117° C.
4-(1-Piperidino)-3-nitrobenzylidenemalonitrile, m.p. 154° C.

EXAMPLE 1

1-Naphthol (1.44 g) was stirred in ethanol (20 ml) at ambient temperature. To this suspension was added 3-(trifluoromethyl)-benzylidenemalononitrile (2.23 g) and piperidine (1 ml). All solids dissolved and heat was evolved. Crystals of 2-amino-4-[3-(trifluoromethyl)-phenyl]-4H-naphtho[1,2-b]pyran-3-carbonitrile came out of solution after a few minutes and were collected by filtration after one hour's further stirring, were washed with ethanol and dried. Recrystallization from ethanol gave white crystals, m.p. 215.5°–216.5° C.

The following compounds were prepared in a similar manner:

EXAMPLE 2

Ethyl 2-amino-4-[3-(trifluoromethyl)phenyl]-4H-naphtho[1,2-b]pyran-3-carboxylate, m.p. 156.5°–157° C.

EXAMPLE 3

Ethyl 2-amino-4-[4-(trifluoromethyl)phenyl]-4H-naphtho[1,2-b]pyran-3-carboxylate, m.p. 124°–126° C.

EXAMPLE 4

Ethyl 2-amino-4-[2-(trifluoromethyl)phenyl]-4H-naphtho [1,2-b]pyran-3-carboxylate, m.p. 144°–146° C.

EXAMPLE 5

2-Amino-4-(2-nitrophenyl)-4H-naphtho[1,2-b]pyran-3-carbonitrile, m.p. 142°–143.5° C.

EXAMPLE 6

2 Amino-4-(3-nitrophenyl)-4H-naphtho[1,2-b]pyran-3-carbonitrile, m.p. 214.5°–216° C.

EXAMPLE 7

2-Amino-4-(4-nitrophenyl)-4H-naphtho[1,2-b]pyran-3-carbonitrile, m.p. 229°–231° C.

EXAMPLE 8

2-Amino-4-[2-(trifluoromethyl)phenyl]-4H-naphtho[1,2-b]pyran-3-carbonitrile m.p. 239°–240° C.

EXAMPLE 9

2-Amino-4-[3-(trifluoromethyl)phenyl]-4H-naphtho[1,2-b]pyran-3-carbonitrile, m.p. 215.5°–216.5° C.

EXAMPLE 10

2-Amino-4-[4-(trifluoromethyl)phenyl]-4H-naphtho[1,2-b]pyran-3-carbonitrile, m.p. 234°–239.5° C.

EXAMPLE 11

2-Amino-6-chloro-4-[3-(trifluoromethyl)phenyl]-4H-naphtho[1,2-b]pyran-3-carbonitrile, m.p. 179°–181° C.

EXAMPLE 12

2-Amino-6-methoxy-4-[3-(trifluoromethyl)phenyl]-4H-naphtho[1,2-b]pyran-3-carbonitrile, m.p. 216°–218° C.

EXAMPLE 13

2-Amino-4-(3-fluorophenyl)-4H-naphtho[1,2-b]pyran-3-carbonitrile, m.p. 240°–242° C.

EXAMPLE 14

2-Amino-4-(3-bromophenyl)-4H-naphtho[1,2-b]pyran-3-carbonitrile, m.p. 234°–235.5° C.

EXAMPLE 15

2-Amino-4-(3-chlorophenyl)-4H-naphtho[1,2-b]pyran-3-carbonitrile, m.p. 226°–228° C.

EXAMPLE 16

2-Amino-4-[4-(2,2-dimethylethyl)phenyl]-4H-naphtho[1,2-b]pyran-3-carbonitrile, m.p. 240°–243° C.

EXAMPLE 17

2-Amino-4-(3-pyridinyl)-4H-naphtho[1,2-b]pyran-3-carbonitrile, m.p. 205°–207° C.

EXAMPLE 18

Ethyl 2-amino-4-(3-nitrophenyl)-4H-naphtho[1,2-b]pyran-3-carboxylate, m.p. 152.5°–153.5° C.

EXAMPLE 19

2-Amino 4-(3-nitrophenyl)-4H-naphtho[1,2-b]pyran-3-carboxamide, m.p. 205°–206.5° C.

EXAMPLE 20

2-Amino-7-methoxy-4-(3-nitrophenyl)-4H-naphtho[1,2-b]pyran-3-carbonitrile, m.p. 242°–246° C.

EXAMPLE 21

2-Amino-8-methoxy-4-(3-nitrophenyl)-4H-naphtho[1,2-b]pyran-3-carbonitrile, m.p. 234°–236° C.

EXAMPLE 22

2-Amino-9-methoxy-4-(3-nitrophenyl)-4H-naphtho[1,2-b]pyran-3-carbonitrile, m.p. 244°–245° C.

EXAMPLE 23

2-Amino-3-cyano-4-(3-nitrophenyl)-4H-naphtho[1,2-b]pyran-6-carboxylic acid, m.p. 244°–248° C.

EXAMPLE 24

2-Amino-3-cyano-4-(3-methoxyphenyl)-4H-naphtho[1,2-b]pyran-6-carboxylic acid, m.p. 280° C. (decomposition).

EXAMPLE 25

2-Amino-3-cyano-4-(3-hydroxyphenyl)-4H-naphtho[1,2-b]pyran-6-carboxylic acid, m.p. 252°–256° C.

EXAMPLE 26

2-Amino-3-cyano-4-[3 (trifluoromethoxy)phenyl]-4H-naphtho[1,2-b]pyran-6-carboxylic acid, m.p. 253°–254.5° C.

EXAMPLE 27

2-Amino-3-cyano-4-(3-carboxyphenyl)-4H-naphtho[1,2-b]pyran-6-carboxylic acid, m.p. >300° C. (decomposition).

EXAMPLE 28

2-Amino-4-(3-methoxyphenyl)-4H-naphtho[1,2-b]pyran-3-30 carbonitrile, m.p. 139°–142.5° C.

EXAMPLE 29

2-Amino-4-(3-carbomethoxyphenyl)-4H-naphtho[1,2-b]pyran-3-carbonitrile, m.p. 235°–236° C.

EXAMPLE 30

2-Amino-4-[3-(trifluoromethoxy)phenyl]-4H-naphtho[1,2-b]pyran-3-carbonitrile, m.p. 194.5°–196.5° C.

EXAMPLE 31

2-Amino-4-(3-chloro-4-fluorophenyl)-4H-naphtho[1,2-b]pyran-3 carbonitrile, m.p. 211°–211.5° C.

EXAMPLE 32

2-Amino-4-(3-bromo-4-fluorophenyl)-4H-naphtho[1,2-b]pyran-3-carbonitrile, m.p. 209.5°–210.5° C.

EXAMPLE 33

2-Amino-7-hydroxy-4-(3-nitrophenyl)-4H-naphtho[1,2-b]pyran-3-carbonitrile, m.p. 237°–239° C.

EXAMPLE 34

2-Amino-4-(4-chloro-3-nitrophenyl)-4H-naphtho[1,2-b]-3-carbonitrile, m.p. 249°–251° C.

EXAMPLE 35

[2-Amino-4-(3-nitrophenyl)-4H-naphtho[1,2-b]pyran-3-yl]methyl sulphone, m.p. 173° C.

EXAMPLE 36

2-Amino-4-(2-nitro-4-thienyl)-4H-naphtho[1,2-b]pyran-3-carbonitrile, m.p. 187°–188° C.

EXAMPLE 37

2-Amino-4-(4-fluoro-3-nitrophenyl)-4H-naphtho[1,2-b]pyran-3-carbonitrile, m.p. 218°–220° C.

EXAMPLE 38

2-Amino-4-(3,4-methylenedioxyphenyl)-4H-naphtho[1,2-b]pyran-3-carbonitrile, m.p. 249°14 252° C.

EXAMPLE 39

2-Amino-4-(3,4-dimethoxyphenyl)-4H-naphtho[1,2-b]pyran-3-carbonitrile, m.p. 207°–209.5° C.

EXAMPLE 40

2-Amino-4-(3,4-dichlorophenyl)-4H-naphtho[1,2-b]pyran-3-carbonitrile, m.p. 247°–249° C.

EXAMPLE 41

3-Nitrobenzaldehyde (84.5 g) and malononitrile (37 g) in ethanol (560 ml) were heated to reflux temperature, with stirring. The heating was halted, piperidine (10 drops) was added and the solution was further heated for 15 minutes. This solution was cooled to 5° C., using an ice-water bath, and to the resultant stirred suspension of intermediate 1-naphthol (80.7 g) was added, followed by piperidine (15 ml). This suspension was heated, under reflux, for 10 minutes and stirred to ambient temperature. The cream crystals of 2-amino-4-(3-nitrophenyl)-4H-naphtho[1,2-b]pyran-3-carbonitrile were filtered off, washed with ethanol until all colour had been removed, and dried, m.p. 214.5°–216° C.

EXAMPLE 42

2-Amino-4-(3 nitrophenyl)-4H-naphtho[1,2-b]pyran-3-carbonitrile (10.3g) was dissolved in dry dimethylformamide (60 ml) and cooled with stirring, to 0° C. in an ice-water bath. Acetyl chloride (12.4 ml) was added, followed by pyridine (14.3 ml). After stirring for three days at ambient temperature the solids that initially had precipitated had redissolved to give a brown viscous solution. This solution was partitioned between brine and chloroform, the chloroform extract was washed with more brine, dried with magnesium sulphate, filtered and evaporated to dryness.

The residue was dissolved in a minimum of chloroform, passed through a 'flash' silica column and chloroform and the fractions containing product were bulked, evaporated and triturated with ether and a little methanol. The yellow 2-diacetylamino-4-(3-nitrophenyl)-4H-naphtho[1,2-b]pyran-3-carbonitrile was filtered off and washed with ether, m.p. 153°–154° C.

The following compound was prepared in a similar manner:

EXAMPLE 43

2-Diacetylamino-4-[3-(trifluoromethyl)phenyl]-4H-naphtho[1,2-b]pyran-3-carbonitrile, m.p. 138.5°–139° C.

EXAMPLE 44

2-Diacetylamino-4-(3-nitrophenyl)-4H-naphtho[1,2-b]pyran-3-carbonitrile (3.62 g) was dissolved in chloroform (200 ml) and mechanically stirred in the presence of Grade III alumina (36 g) for 24 hours at ambient temperature. The suspension was filtered, the alumina pad was washed through with 5% methanol in chloroform, the combined filtrates were evaporated and the residue was triturated with a little chloroform. The white solid was dissolved in dioxan (50 ml) and left to stand for 24 hours. An impurity precipitated out and this was filtered off. Water was added (200 ml) to the filtrate and the solid produced was filtered off, washed with water and dried. This solid was passed through a chloroform—'flash' silica column. The fractions containing product were bulked, evaporated to dryness and triturated with methanol to give yellow crystals of 2-acetamido-4-(3-nitrophenyl)-4H-naphtho[1,2-b]pyran-3-carbonitrile, m.p. 234.5°–236° C.

EXAMPLE 45

2-Amino 4 (3-chloro-4-fluorophenyl)-4H-naphtho[1,2-b]pyran-3-carbonitrile (3.12 g) was heated, under reflux, in triethyl orthoformate (40 ml) for 24 hours. A fraction coming over at 80° to 140° C. was distilled off and more triethyl orthofomate (40 ml) was added, and the refluxing was continued for a further 24 hours. The solution was evaporated to dryness. The gummy residue was dissolved in chloroform and passed through a column of 'flash' silica using 30% hexane in chloroform as eluant. The fractions containing product were bulked, evaporated and triturated with ethyl acetate to give white crystals of 4-(3-chloro-4-fluorophenyl)-2-ethoxymethyleneamino-4H-naphtho[1,2-b]pyran-3-carbonitrile, m.p. 146°–148° C.

Similarly produced were:

EXAMPLE 46

2-Ethoxymethyleneamino-4-(3-nitrophenyl)-4H-naphtho[1,2-b]pyran-3-carbonitrile, m.p. 181.5°–183° C.

EXAMPLE 47

4-(4-Chloro-3-nitrophenyl)-2-ethoxymethyleneamino-4H-naphtho[1,2-b]pyran-3-carbonitrile, m.p. 184.5°–186° C.

EXAMPLE 48

2-Amino-4-(4-chloro-3-nitrophenyl)-4H-naphtho[1,2-b]pyran-3-carbonitrile (3.8 g) was dissolved in tetrahydrofuran (30 ml), at room temperature. To this was added pyridine (2.02 ml) followed by succinyl chloride (1.34 ml) and the solution was stirred for 24 hours. More pyridine (2.02 ml) and succinyl chloride (1.34 ml) was added. The solution was heated under reflux for 6 hours, cooled, poured into water and partitioned into chloroform. The chloroform extract was washed with brine, dried with magnesium sulphate, passed through a column of silica gel using 30% hexane in chloroform as eluant, evaporated to dryness and triturated with ethyl acetate to give 1.07 g of 4-(4-chloro-3-nitrophenyl)-2-(N-succinimido)-4H-naphtho[1,2-b]pyran-3-carbonitrile, m.p. 215.5°–217° C.

EXAMPLE 49

4-(4-Chloro-3-nitrophenyl)-2-ethoxymethyleneamino-4H-naphtho[1,2-b]pyran-3-carbonitrile (4.3 g) was dissolved in tetrahydrofuran (70 ml), and to this solution, with stirring, was added sodium borohydride (2.7 g), in portions. After one hour the suspension was cooled in ice-water and 1 molar hydrochloric acid (20 ml) was added dropwise, followed by water (200 ml). A yellow product was filtered off, washed with water and dried. This material was dissolved in hot chloroform and passed down a chloroform—'flash silica' column. Fractions containing product were bulked, evaporated to dryness, and triturated with ether to give 4-(4-chloro-3-nitrophenyl)-2-methylamino-4H-naphtho[1,2-b]pyran-3-carbonitrile, m.p. 278.5°–279° C.

EXAMPLE 50

2-Amino-4-(4-chloro-3-nitrophenyl)-4H-naphtho[1,2-b]pyran-3-carbonitrile (3.8 g) was dissolved in 2-butanone (100 ml). To this stirred solution was added dimethyl sulphate (2.4 ml) and potassium carbonate (3.5 g). This suspension was heated under reflux for two hours. More dimethyl sulphate (2.4 ml) and potassium carbonate (3.5 g) were added. The solution was heated for an additional 22 hours, cooled, filtered, evaporated to dryness, the residue was dissolved in warm chloroform and passed through a 'flash' chromatography column using 20% hexane-chloroform (1 liter) then further eluted with 10% hexane-chloroform (1 liter). The elution was then completed using chloroform. The fractions containing product were bulked, evaporated to dryness and the residue triturated with diethyl ether. Recrystallization from toluene gave yellow crystals of 4-(4-chloro-3-nitrophenyl)-2-dimethylamino-4H-naphtho[1,2-b]pyran-3-carbonitrile, m.p. 217.5°–218.5° C.

EXAMPLE 51

4-(4-Chloro-3-nitrophenyl)-2-(N-succinimido)-4H-naphtho[1,2-b]pyran-3-carbonitrile (0.41 g) was dissolved in tetrahydrofuran (20 ml). To this solution 2M sodium hydroxide was added (0.94 ml) and the solution was stirred for two days, at ambient temperature. The solution was evaporated to dryness and the residue was dissolved in water (50 ml) and filtered. To the filtrate acetic acid (1.14 ml) was added and the precipitated buff N-[4-(4-chloro-3-nitrophenyl)-3-cyano-4H-naphtho[1,2-b]pyran-2-yl]-succinamic acid was filtered off, washed with water and dried, m.p. >300° C.

As previously indicated these compounds are useful for the treatment of diabetic complications. The activity of the compounds of the present invention was identified through in vitro studies using activated endothelial cells.

Retinal capillary endothelial cell cultures were initiated from bovine eyes using a modification of the procedure of Buzney et al., *Investigative Ophthalmology and Visual Sciences*, 24: 470–480 (1983). Bovine eyes were transported on ice from a local abattoir. Extraocular muscle was trimmed from the eye, and the eye bisected posterior to the ora serrata. The vitreous and anterior portion of the eye were discarded, and the neuro-retina was gently dissected from the posterior eyecup. The retinas from 20 cattle were pooled and homogenized (5 strokes of a Teflon/glass homogenizer) in Hank's saline. The homogenate was passed through a 350μ filter to remove large debris and a 210μ filter to remove large vessels. The microvessels were trapped on a 85μ filter. The microvessels were resuspended in Hank's saline and digested with 7.5 mg/ml bacterial collagenase (Boeringher Mannheim, Indianapolis) Hank's saline for 1 hour at 37° C. The cells were pelleted by centrifugation (100 xg, 10 min), resuspended in 5 ml Endothelial Growth Media (EGM, Clonetics) and seeded in a gelatin-coated T-25 flask. After 24 hours the cells were trypsinized and replated in a gelatin coated T225. At 7 days and again at 14 days the cultures were labeled with acetylated lipoproteins labeled with the fluorescent probe (1,1'-dioctadecyl-3,3,3,3,-tetramethyl-indocarbocyanine perchlorate). The endothelial cells were separated from contaminating cell types using a fluorescent cell sorter as described in Voyta et al., *J. Cell Biology*, 99: 2034–2040 (1984).

Retinal capillary endothelial cells were seeded into 96-well plates and grown to confluence ($10^5$ cells/well) in EGM containing 10% fetal bovine serum (FBS). The media was changed to Dubecco's Modified Eagle's Medium with 10% fetal bovine serum 24 hours prior to the assay. The cells were treated with 50 nM 4-$\beta$ phorbol 12,13-dibutyrate (4-$\beta$ PDBu) to activate PKC and produce the activated endothelial phenotype characteristic of the diabetic state. The activated cells were treated with a series of dilutions of the test compounds. The phorbol esters and the test compounds were dissolved in DMSO before adding to the culture media. The cultures were incubated at 37° C. for 48 hours. Following treatment, the cells were lysed with 25mM NH$_4$OH in 0.5% triton X-100.

The activation of bovine retinal capillary endothelial cells was monitored through alterations in cellular plasminogen activator (PA) activity in the cell lysates. Plasminogen activator activity was determined in a 50 $\mu$l aliquot of cell lysate using the synthetic substrate H-D-valyl-L-leucyl-lysine-p-nitroaniline dihydrochloride (Kabi).

Treatment of confluent bovine retinal capillary endothelial cells for 48 hours with PDBu resulted in a 12 fold increase in PA activity associated with the cell layer and a 12 fold increase in PA released into the media. There was also a two fold increase in cell number. This increase in activation occurred only after treatment with phorbol esters known to activate PKC (4-$\beta$ PDBu, 4-$\beta$ PMA, but not 4-$\alpha$ PDBu, 4-$\alpha$ PMA). No cleavage of the synthetic substrate was observed when plasminogen was omitted from the assay mixture, indicating that the increase in activity observed in phorbol treated cultures was restricted to activators of plasminogen. Dose-response curves generated for 4-$\beta$ PDBu and 4-$\beta$ PMA indicated IC$_{50}$s of 50 nM and 5 nM respectively. Elevated PA activity was observed only after prolonged (at least 8 hours) stimulation with phorbol esters. The PA activity continued to increase in a time and dose dependent manner for up to 72 hours, but constant stimulation with phorbol ester was required to maintain endothelial cell activation. Removal of the phorbol ester resulted in a rapid return of PA activity to normal levels.

Cell toxicity was determined in a parallel series of cultures using a neutral red assay. Borenfreund, E. and Puerner, J, *J. Tiss. Cult. Meth.* 9: 7 (1984). The effectiveness of the present compounds to inhibit endothelial cell activation was found to be distinct from cell toxicity. In general, the compounds of the present invention were shown to be effective in inhibiting the endothelial cell activation induced by phorbol esters and have a PA IC$_{50}$ value in this test below 10 $\mu$M.

The results illustrated in Table 1 indicate that representative compounds are potent inhibitors of endothelial cell activation.

TABLE 1

| Compound (Example Number) | PA IC$_{50}$ |
| --- | --- |
| 6 | 0.025 $\mu$M |
| 5 | 0.50 $\mu$M |

Representative compounds were evaluated in situ for their ability to block the increase in blood flow and permeability induced by high glucose in a rat tissue granulation tissue chamber model. In this model circles of skin were removed from the backs of normal rats and stainless steel screw-cap chambers were mounted. New granulation tissue formed within the chambers. Addition of 30–35 mM glucose (0.5 ml) twice daily to the chambers for 7 days induced a vascular dysfunction similar to that of diabetes—that is there was an increase in blood vessel permeability and an increase in blood flow. Blood flow was measured through the use of radiolabeled microspheres, and permeability was quantified using a dual label technique with iodinated albumin ($^{125}$I/$^{131}$I). Details of the model can be found in Tilton, et al., *Diabetes* 38: 1258–1270 (1989). and Williamson, et al., *J. Clin. Invest.* 85: 1167–1172 (1990).

Representative compounds were dissolved in DMSO and diluted in a balanced salt solution to achieve a final concentration of 20 or 50 $\mu$M. The granulation chamber tissue was treated twice daily for 7 days to determine their effects on glucose-induced vascular dysfunction. Addition of 30–35 mM glucose to the granulation chamber induced a vascular dysfunction characterized by increased vessel permeability and increased blood flow. Table 2 demonstrates activity of representative compounds in the granulation chamber model.

TABLE 2

| Pyrans Block Glucose-Induced Vascular Dysfunction in Normal Rats | | | |
| --- | --- | --- | --- |
| Compound (Example Number) | Concentration ($\mu$M) | BSA Clearance (g/g/min) | Blood Flow (ml/g/min) |
| 6 | 20 | 179 | 0.184 |
| 6 | 50 | 158 | 0.168 |
| 5 | 20 | 163 | 0.231 |
| Control: Glucose | 30 | 412 | 0.449 |

These results indicate that the compounds are capable of preventing glucose-induced vascular dysfunction in the rat. The results also indicate a good correlation between the cell-based activities tested in vitro and the in situ activities.

Representative compounds were further evaluated for their ability to block the microvascular dysfunction associated with streptozotocin-induced diabetes. Rats were made diabetic with an injection of streptozotocin, and the rats were feed ad libitum with a diet containing 0.1% of a representative compound. Blood flow was measured through the use of radiolabeled microspheres while permeability was quantified using a dual label technique with iodinated albumin ($^{125}$I/$^{131}$I). Details of the model can be found in Tilton et al., *Diabetes* 38: 1258–1270 (1989), and Williamson et al., *J. Clin. Invest.* 85: 1167–1172 (1990).

The induction of diabetes in rats resulted in a significant increase in permeability in the retina, nerve and aorta. Blood flow also was elevated on induction of diabetes in these tissues. In contrast, vascular function was not affected in the brain or muscle. As illustrated by Table 3, the supplementation of the diet (0.1%) with the compound of Example 6 of the present invention prevented the development of increased permeability and blood flow in the vasculature in streptozotocin-diabetic rats over a 4 to 7-week period.

TABLE 3

| | Permeability (μg/g/min) | | |
|---|---|---|---|
| | Control | Diabetic | Compound |
| Retina | 58.00 | 117.00 | 59.00 |
| Nerve | 61.00 | 116.00 | 63.00 |
| Aorta | 86.00 | 184.00 | 99.00 |
| Muscle | 62.00 | 46.00 | 63.00 |
| Brain | 25.00 | 22.00 | 19.00 |

TABLE 4

| | Blood Flow (ml/min/g) | | |
|---|---|---|---|
| | Control | Diabetic | Compound |
| Retina | 0.39 | 0.45 | 0.40 |
| Nerve | 0.06 | 0.10 | 0.05 |
| Brain | 0.58 | 0.65 | 0.88 |

The compounds may be administered by various routes, for example, by the oral or rectal route, topically or parenterally, for example by injection, being usually employed in the form of a pharmaceutical composition. Such compositions are prepared in a manner well known in the pharmaceutical art and normally comprise at least one active compound in association with a pharmaceutically-acceptable diluent or carrier. In making the compositions, the active ingredient will usually be mixed with a carrier, or diluted by a carrier, and/or enclosed with a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc magnesium stearate and mineral oil. The compositions of the injection may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way.

The term "treating" includes the administration of a compound of the present invention to prevent the onset of the symptoms, alleviating the symptoms, or eliminating the disease, condition or disorder.

We claim:

1. A method of treating diabetic complications, which comprises administering to a patient in need of treatment a therapeutic dosage of a compound of the Formula (I):

wherein
n is 0, 1 or 2;
$R^1$ is $C_1$-$C_4$ alkoxy, OH, or COOH attached at any of the positions 5, 6, 7, 8, or 9;
$R^2$ is phenyl, said phenyl being optionally substituted;
$R^3$ is nitrile, or $R_3$ is carboxy or —$COOR_8$ when $R_2$ is phenyl substituted with 3-nitro or 3-trifluoromethyl;
$R^4$ is —$NR^{12}R^{13}$, —$NHCOR^{12}$, —$N(COR^{12})_2$, or —$N=CHOCH_2R^{12}$;
$R^8$ is an ester group; and
$R^{12}$ and $R^{13}$ are each hydrogen or $C_{1-4}$ alkyl.

2. A method according to claim 1 wherein n is 1 and $R^1$ is $C_{1-4}$ alkoxy.

3. A method according to claim 2 wherein $R^2$ is phenyl substituted with one or two substituents selected from halo, nitro or trifluoromethyl.

4. A method according to claim 3 wherein $R^3$ is nitrile.

5. A method according to claim 4 wherein $R^4$ is —$NH_2$.

6. A method of inhibiting endothelial cell activation, which comprises administering to a patient in need of treatment a therapeutic dosage of a compound of the Formula I:

wherein
n is 0, 1 or 2;
$R^1$ is $C_1$-$C_4$ alkoxy, OH, or COOH attached at any of the positions 5, 6, 7, 8, or 9;
$R^2$ is phenyl, said phenyl being optionally substituted;
$R^3$ is nitrile, or $R_3$ is carboxy or —$COOR_8$ when $R_2$ is phenyl substituted with 3-nitro or 3-trifluoromethyl;

$R^4$ is $-NR^{12}R^{13}$, $-NHCOR^{12}$, $-N(COR^{12})_2$, or $-N=CHOCH_2R^{12}$;

$R^8$ is an ester group; and $R^{12}$ and $R^{13}$ are each hydrogen or $C_{1-4}$ alkyl.

7. A method of treating vascular dysfunction, which comprises administering to a patient in need of treatment a therapeutic dosage of a compound of the Formula I:

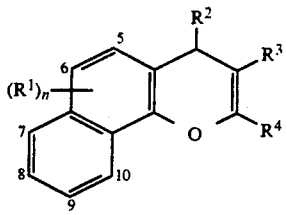

(I)

wherein
n is 0, 1 or 2;
$R^1$ is $C_1$-$C_4$ alkoxy, OH, or COOH attached at any of the positions 5, 6, 7, 8, or 9;
$R^2$ is phenyl, said phenyl being optionally substituted;
$R^3$ is nitrile, or $R_3$ is carboxy or $-COOR_8$ when $R_2$ is phenyl substituted with 3-nitro or 3-trifluoromethyl;
$R^4$ is $-NR^{12}R^{13}$, $-NHCOR^{12}$, $-N(COR^{12})_2$, or $-N=CHOCH_2R^{12}$;
$R^8$ is an ester group; and
$R^{12}$ and $R^{13}$ are each hydrogen or $C_{1-4}$ alkyl.

* * * * *

UNITED STATES PATENT AND TRADEMARK OFFICE
CERTIFICATE OF CORRECTION

PATENT NO. : 5,281,619
DATED : January 25, 1994
INVENTOR(S) : Colin P. Dell et al It is certified that error appears in the above-indentified patent and that said Letters Patent is hereby corrected as shown below:

Column 14, line 27, delete "8,".

Column 14, line 64, delete "8,".

Column 16, line 15, delete "8,".

Signed and Sealed this

Twenty-first Day of June, 1994

Attest:

BRUCE LEHMAN

*Attesting Officer*   *Commissioner of Patents and Trademarks*